United States Patent
Ross

(10) Patent No.: US 10,028,769 B2
(45) Date of Patent: Jul. 24, 2018

(54) GYNOCOLOGICAL CERVICAL OS INSTRUMENT

(71) Applicant: Sheryl A Ross, Santa Monica, CA (US)

(72) Inventor: Sheryl A Ross, Santa Monica, CA (US)

(*) Notice: Subject to any disclaimer, the term of this patent is extended or adjusted under 35 U.S.C. 154(b) by 331 days.

(21) Appl. No.: 14/535,121

(22) Filed: Nov. 6, 2014

(65) Prior Publication Data

US 2016/0128728 A1 May 12, 2016

(51) Int. Cl.
*A61B 17/42* (2006.01)
*A61B 17/34* (2006.01)
*A61B 17/00* (2006.01)

(52) U.S. Cl.
CPC .......... *A61B 17/42* (2013.01); *A61B 17/3415* (2013.01); *A61B 2017/0042* (2013.01); *A61B 2017/00853* (2013.01); *A61B 2017/345* (2013.01)

(58) Field of Classification Search
CPC ............ A61B 17/42; A61B 2017/4216; A61B 2017/4225
See application file for complete search history.

(56) References Cited

U.S. PATENT DOCUMENTS

| | | | |
|---|---|---|---|
| 512,024 A | 1/1894 | Haviland | |
| 3,385,300 A | 5/1968 | Holter | |
| 3,467,088 A | 9/1969 | Robinson | |
| 3,506,010 A * | 4/1970 | Murr | A61M 1/008 604/151 |
| 3,704,712 A | 12/1972 | Giesy | |
| 3,771,520 A | 11/1973 | Lerner | |
| 3,927,666 A | 12/1975 | Hoff | |
| 4,553,543 A * | 11/1985 | Amarasinghe | A61B 17/04 606/148 |
| 4,662,381 A | 5/1987 | Inaba | |
| 4,911,164 A * | 3/1990 | Roth | A61B 17/3403 606/148 |
| 5,144,942 A * | 9/1992 | Decarie | A61B 1/00144 206/363 |
| 5,147,315 A | 9/1992 | Weber | |
| 6,071,230 A * | 6/2000 | Henalla | A61B 17/062 600/29 |

(Continued)

FOREIGN PATENT DOCUMENTS

| | | |
|---|---|---|
| CN | 2933448 | 8/2007 |
| SU | 1109176 | 8/1984 |

*Primary Examiner* — Tuan V Nguyen
(74) *Attorney, Agent, or Firm* — Duane Morris LLP

(57) ABSTRACT

A gynocological cervical Os instrument. The gynecological cervical Os instrument includes a cervical Os finder having a passage for another medical instrument at least partially along the Os finder's length. In some aspects, the passage is only partially along the Os finder's length. The passage may be a groove, and the gynecological cervical Os instrument may include one or more retainers across the groove for the medical instrument. The gynecological cervical Os instrument may include a ramp out of the passage at the end of the passage and one or more bumps on the other end of the gynecological cervical Os instrument opposite the ramp indicative of a size of the gynecological cervical Os instrument. The gynecological cervical Os instrument may be made of a thermoplastic polymer such as polytetrafluoroethylene.

14 Claims, 3 Drawing Sheets

(56) References Cited

U.S. PATENT DOCUMENTS

| | | | |
|---|---|---|---|
| 6,283,948 B1* | 9/2001 | McKernan | A61B 17/3417 604/272 |
| 6,669,643 B1* | 12/2003 | Dubinsky | A61B 10/04 600/459 |
| 6,733,515 B1* | 5/2004 | Edwards | A61B 17/00491 604/264 |
| 7,604,640 B2* | 10/2009 | Kana | B25B 19/00 173/1 |
| 2001/0047147 A1* | 11/2001 | Slepian | A61B 17/32072 604/22 |
| 2003/0195524 A1 | 10/2003 | Barner | |
| 2004/0162461 A1* | 8/2004 | Christine | A61B 17/43 600/35 |
| 2006/0122566 A1 | 6/2006 | Huang et al. | |
| 2007/0043264 A1* | 2/2007 | Gillis | A61B 1/303 600/184 |
| 2007/0173736 A1 | 7/2007 | Feuer et al. | |
| 2007/0270885 A1* | 11/2007 | Weinert | A61B 17/0469 606/139 |
| 2007/0289415 A1* | 12/2007 | Hsieh | B25B 13/04 81/177.1 |
| 2008/0045924 A1* | 2/2008 | Cox | A61B 10/0045 604/515 |
| 2010/0106163 A1* | 4/2010 | Blair | A61B 17/4241 606/119 |
| 2010/0222744 A1 | 9/2010 | Riek et al. | |
| 2015/0105792 A1* | 4/2015 | Adams | A61B 17/42 606/119 |

\* cited by examiner

GYNOCOLOGICAL CERVICAL OS INSTRUMENT

CROSS-REFERENCE TO RELATED APPLICATION

Not applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND

The present disclosure generally relates to a gynecological cervical Os instrument.

SUMMARY

Gynecologists often need to access a patient's uterus through the opening in the patient's cervix. This opening may be referred to as the cervical Os. Examples of procedures that involve accessing the patient's uterus through the cervical Os include but are not limited to endometrial biopsies and Intra-uterine Inseminations (IUIs). Unfortunately, existing medical instruments for performing these and other procedures suffer from various inadequacies as explained below, especially in the cases of patients with certain fairly normal anatomical variations such as anteverted or retroverted uteruses or cervical stenosis. The subject technology attempts to address these inadequacies.

Aspects of the subject technology include a gynecological cervical Os instrument that includes a cervical Os finder having a passage for another medical instrument at least partially along the Os finder's length. In some aspects, the passage is only partially along the Os finder's length. The passage may be a groove, and the gynecological cervical Os instrument may include one or more retainers across the groove to help hold the other medical instrument in place.

The gynecological cervical Os instrument may include a ramp out of the end of passage and one or more bumps on the other end of the gynecological cervical Os instrument opposite the ramp indicative of a size of the gynecological cervical Os instrument. The gynecological cervical Os instrument may also include a thumb and/or index finger depression. The instrument may be made of a thermoplastic polymer such as polytetrafluoroethylene.

This brief summary has been provided so that the nature of the invention may be understood quickly. Additional steps and/or different steps than those set forth in this summary may be used. A more complete understanding of the invention may be obtained by reference to the following description in connection with the attached drawings.

DETAILED DESCRIPTION

Gynecologists often need to access a patient's uterus through the opening in the patient's cervix. This opening may be referred to as the cervical Os. Examples of procedures that involve accessing the patient's uterus through the cervical Os include but are not limited to endometrial biopsies and Intra-uterine Inseminations (IUs). Unfortunately, existing medical instruments for performing these and other procedures suffer from various inadequacies.

For example, in the case of patients with anteverted, retroverted, or mid-position uteruses, locating the cervical Os may be difficult. Once the cervical Os is located, a gynecologist may have to dilate the cervical Os with a cervical dilator, remove the dilator, and then quickly insert another medical instrument such as an endometrial pipelle or a Tom Catheter before the cervical Os closes or collapses to its original diameter.

Requiring haste in a medical procedure is undesirable. For example, haste when inserting the other medical instrument has been known to result in perforation of the cervical or uterine walls. Such perforation has resulted in significant negative medical consequences for patients. Similar problems have arisen with patients who have cervical stenosis.

Even if perforation does not occur, the cervical Os may close or collapse to its original diameter before the other medical instrument can be properly inserted into the patient's uterus. As a result, the patient's cervical Os may have to be re-dilated, extending the procedure and possibly resulting in significant patient discomfort. This too is undesirable.

The subject technology attempts to address the foregoing inadequacies that may result from using conventional gynecological instruments.

Briefly, aspects of the subject technology include a gynecological cervical Os instrument that includes a cervical Os finder having a passage for another medical instrument at least partially along the Os finder's length. In some aspects, the passage is only partially along the Os finder's length. The passage may be a groove, and the gynecological cervical Os instrument may include one or more retainers across the groove to help hold the other medical instrument in place.

The gynecological cervical Os instrument may include a ramp out of the end of the passage and one or more bumps on the other end of the gynecological cervical Os instrument opposite the ramp indicative of a size of the gynecological cervical Os instrument. The gynecological cervical Os instrument may also include a thumb and/or index finger depression. The instrument may be made of a thermoplastic polymer such as polytetrafluoroethylene. These and other aspects of the subject technology are described below with reference to the figures.

Figure 1:
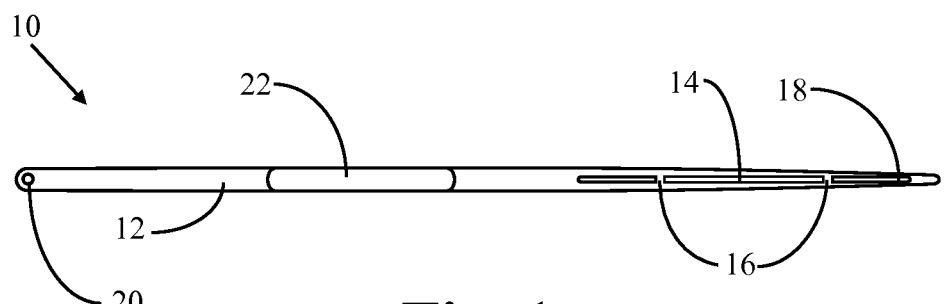
FIG. 1 illustrates a top view of a gynecological cervical Os instrument according to aspects of the subject technology.

FIG. 1 illustrates a top view of a gynecological cervical Os instrument according to aspects of the subject technology. Gynecological cervical Os instrument 10 includes cervical Os finder 12 having passage 14 for another medical instrument at least partially along the finder's length. Examples of such other instruments include but are not limited to endometrial pipelles and Tom Catheters. In FIG. 1, passage 14 is only partially along the finder's length. However, the passage may be along the entire length of finder 12 according to the subject technology.

Passage 14 in FIG. 1 takes the form of a groove. Other types of passages may be used, for example a bored or cast tunnel through finder 12. The passage may also be through the entire instrument. However, such an arrangement may lead to a less ergonomic arrangement for use of the gynecological cervical Os instrument along with the other medical instrument.

The main portion of the passage preferably has a diameter of 3.3 or 3.4 millimeters to accommodate typical endometrial pipelles and Tom Catheters. However, the passage may be larger or smaller to accommodate other medical instruments.

The width of the main portion of instrument 10 preferably is slightly larger than the passage, for example 3.8 millimeters. The end of instrument 10 preferably tapers, for example to 1.75 millimeters, in order to facilitate guidance of gynecological cervical Os instrument 10 through smaller or tighter cervical Os, cervical stenosis, or the like. The passage preferably also narrows toward the end of instrument 10, which may facilitate passage of the other medical instrument out of the groove and into a patient's uterus.

The gynecological cervical Os instrument illustrated in FIG. 1 also includes two retainers 16 across the groove to help hold the other medical instrument in place. Fewer (e.g., none or one) or more (e.g., three or more) such restrainers may be included according to aspects of the subject technology.

The instrument in FIG. 1 also illustrates ramp 18 out of passage 14. This ramp facilitates access to a patient's uterine wall when instrument 10 is in place through a patient's cervical Os into the patient's uterus. As noted earlier, this ramp may be narrow as compared to the rest of passage 14, which may facilitate passage of the other medical instrument out of the groove and into the patient's uterus.

The sizes of the cervical Os and uteruses varies among patients. Therefore, gynecologists may need to use different sizes of gynecological cervical Os instrument 10 for different patients. The use of the wrong sized instrument may lead to patient discomfort and/or difficulty in accessing the patient's uterus. The present technology addresses this issue by including one or more bumps 20 indicative of a size of instrument 10. A gynecologist may tactilely feel the size of instrument 10 in his or her grasp by virtue of bump 20.

Instrument 10 in FIG. 1 also includes thumb depression 22 and an index finger depression (shown as depression 24 in FIG. 3), which may enhance a gynecologists control when using the instrument. While these features are preferred, they are not essential to the subject technology.

In preferred aspects, gynecological cervical Os instruments according to the subject technology may be made from any suitable medically appropriate material. Examples include but are not limited to surgical steel, thermoplastic polymers such as polytetrafluoroethylene (PTFE aka TEFLON®), and the like. PTFE is preferred due to its durability and flexibility, which may reduce patient discomfort during use.

Figure 2:
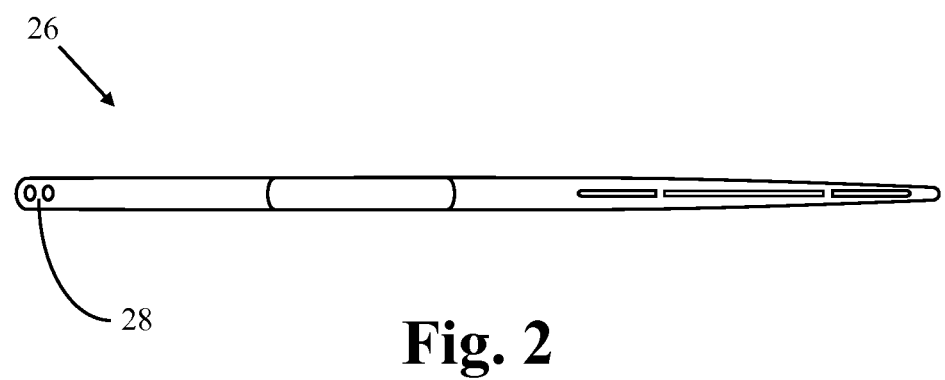
FIG. 2 illustrates a top view of a larger gynecological cervical Os instrument according to aspects of the subject technology.

FIG. 2 illustrates a top view of a larger gynecological cervical Os instrument according to aspects of the subject technology. Instrument 26 is larger than instrument 10 in FIG. 1. Thus, the instrument include two bumps 28 versus one bump 20 in FIG. 1, indicating its larger size. Larger gynecological cervical Os instruments according to aspects of the subject technology may include more bumps to tactilely indicate their size.

Figure 3:
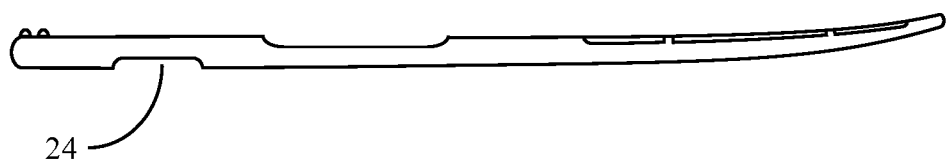
FIG. 3 illustrates a side view of a gynecological cervical Os instrument according to aspects of the subject technology.

FIG. 3 illustrates a side view of a gynecological cervical Os instrument shown in FIG. 2. Index depression 24 may be seen in this figure.

Figure 4:
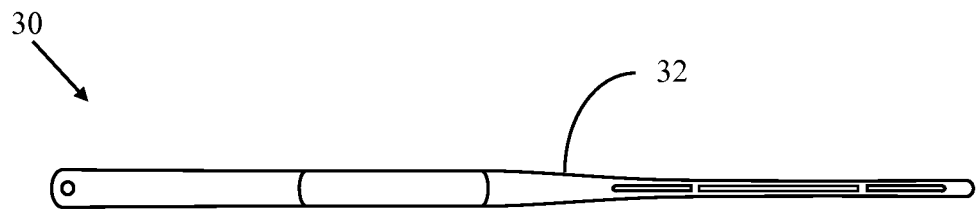
FIG. 4 illustrates a top view of a gynecological cervical Os instrument according to aspects of the subject technology.

FIG. 4 illustrates a top view of a gynecological cervical Os instrument according to aspects of the subject technology. This instrument 30 includes widening 32, which may help to prevent over-insertion of the instrument.

Figure 5:
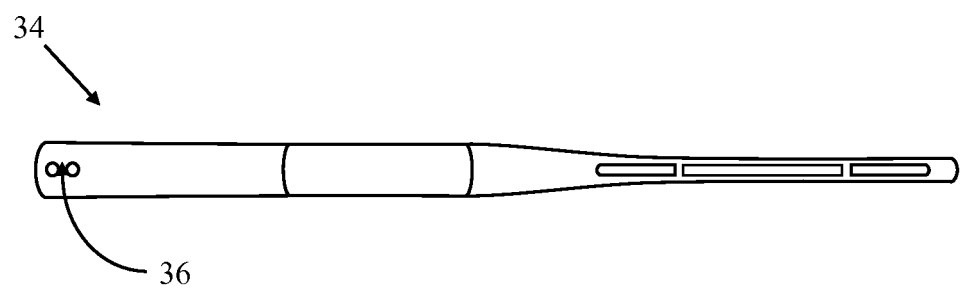
FIG. 5 illustrates a top view of a larger gynecological cervical Os instrument according to aspects of the subject technology.

FIG. 5 illustrates a top view of a larger gynecological cervical Os instrument according to aspects of the subject technology. Instrument 34 is larger than instrument 30 and therefore has two bumps 36 to indicate its larger size.

Figure 6:
FIG. 6 illustrates a side view of a gynecological cervical Os instrument according to aspects of the subject technology.

FIG. 6 illustrates a side view of a gynecological cervical Os instrument shown in FIG. 5.

Figure 7:
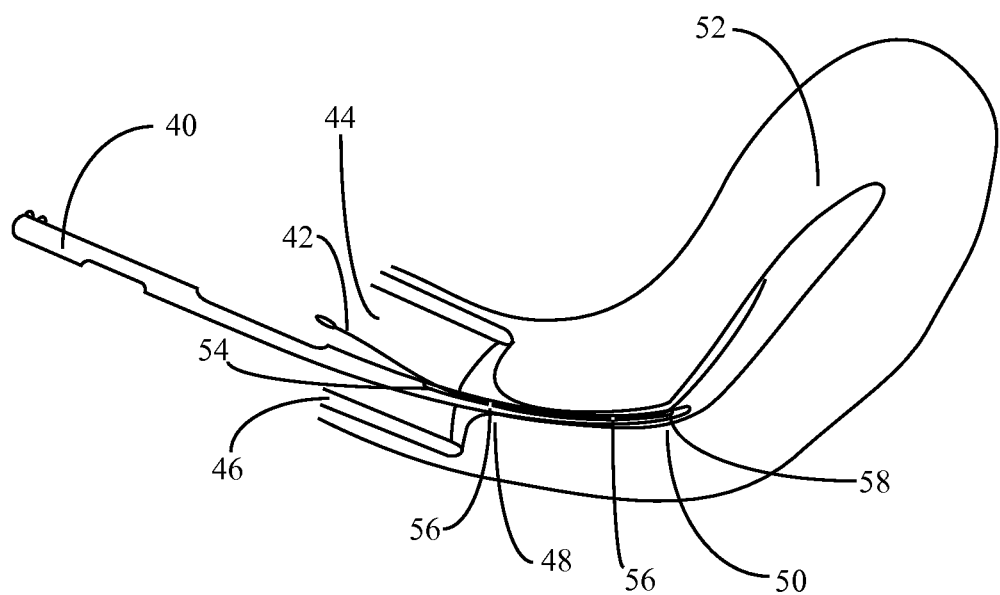
FIG. 7 illustrates a gynecological cervical Os instrument according to aspects of the subject technology in use.

FIG. 7 illustrates one possible use of a gynecological cervical Os instrument according to aspects of the subject technology. Gynecological cervical Os instrument 40 is being used to perform a procedure in conjunction with pipelle 42. In more detail, a patient's vaginal canal 44 is being held open with speculum 46. Instrument 40 according to aspects of the subject technology has passed through the patients external Os 48 and internal Os 50. Pipelle 42 has been inserted into uterus 52 along groove 54 of instrument 40. Retainers 56 have helped guide pipelle 42 through the patient's cervix. The pipelle has penetrated into the patient's uterus after exiting instrument 40 as guided by ramp 58. The pipelle may then be removed after the procedure is finished. Other medical instruments for other procedures may also be inserted before the gynecological Os cervical instrument 40 is removed.

Gynecological Os cervical instrument 40 also may be removed while leaving pipelle 42 or another medical instrument such as a Tom Catheter in place once the other medical instrument has been properly inserted into the patient's uterus. Because instrument 40 has a larger diameter than the other medical instrument, removal of gynecological Os cervical instrument 40 may decrease patient discomfort.

The invention is in no way limited to the specifics of any particular embodiments and examples disclosed herein. For example, the terms "aspect," "example," "preferably," "alternatively" and the like denote features that may be preferable but not essential to include in some embodiments of the invention. In addition, details illustrated or disclosed with respect to any one aspect of the invention may be used with other aspects of the invention. Additional elements may be added to various aspects of the invention and/or some disclosed elements may be subtracted from various aspects of the invention without departing from the scope of the invention. Singular elements imply plural elements and vice versa. Many other variations are possible which remain within the content, scope and spirit of the invention, and these variations would become clear to those skilled in the art after perusal of this application.

What is claimed is:

1. A system for facilitating access to a patient's uterus, comprising:

a cervical Os finder having a passage extending along a distal portion of the finder's length and ending before reaching a proximal portion of the finder's length configured to be held by a user, wherein the passage is configured to receive at least a portion of a second medical instrument therein, the finder further comprising a tapered leading portion configured to penetrate the cervical Os of a patient and gradually increase dilation of the cervical Os as the leading portion is inserted further into the cervical Os; and an endometrial biopsy device having at least a portion thereof configured to pass through the passage and into the patient's uterus, and wherein the passage allows at least a portion of the endometrial biopsy device to pass through the cervical Os and enter the uterus of the patient while the leading portion remains inserted in the cervical Os, wherein the passage comprises a groove and a ramp located at an end of the groove near a tip of the leading portion, wherein the ramp is configured to facilitate access to the patient's uterine cavity or wall by the second medical instrument, wherein the second medical instrument comprises the endometrial biopsy device.

2. The system of claim 1, further comprising at least one retainer configured to retain the second medical instrument within the groove.

3. The system of claim 2, further comprising at least a second retainer configured to retain the second medical instrument within the groove.

4. The system of claim 1, further comprising one or more bumps on an end of the cervical Os finder opposite the ramp indicative of a size of the cervical Os finder.

5. The system of claim 1, wherein the cervical Os finder comprises polytetrafluoroethylene.

6. The system of claim 1, further comprising a thumb depression located on an end of the cervical Os finder opposite the ramp.

7. The system of claim 6, further comprising an index finger depression located on an end of the cervical Os finder opposite the ramp.

8. A system for facilitating access to a patient's uterus, comprising:

a cervical Os finder having a passage extending along a distal portion of the finder's length and ending before reaching a proximal portion of the finder's length configured to be held by a user, wherein the passage is configured to receive at least portion of a second medical instrument therein, the finder further comprising a tapered leading portion configured to penetrate the cervical Os of a patient and gradually increase dilation of the cervical Os as the leading portion is inserted further into the cervical Os; and a catheter having at least a portion thereof configured to pass through the passage and into the patient's uterus, and wherein the passage allows at least a portion of the catheter to pass through the cervical Os and enter the uterus of the patient while the leading portion remains inserted in the cervical Os, wherein the passage comprises a groove and a ramp located at an end of the groove near a tip of the leading portion, wherein the ramp is configured to facilitate access to the patient's uterine cavity or wall by the second medical instrument.

9. The system of claim 8, further comprising at least one retainer configured to retain the second medical instrument within the groove.

10. The system of claim 9, further comprising at least a second retainer configured to retain the second medical instrument within the groove.

11. The system of claim 8, further comprising one or more bumps on an end of the cervical Os finder opposite the ramp indicative of a size of the cervical Os finder.

12. The system of claim 8, wherein the cervical Os finder comprises polytetrafluoroethylene.

13. The system of claim 8, further comprising a thumb depression located on an end of the cervical Os finder opposite the ramp.

14. The system of claim 13, further comprising an index finger depression located on an end of the cervical Os finder opposite the ramp.

* * * * *